United States Patent [19]

Koyama et al.

[11] 4,388,318

[45] Jun. 14, 1983

[54] METHOD OF TREATING ENDOTOXIN SHOCK WITH A PYRIMIDO-PYRIMIDINE DERIVATIVE

[75] Inventors: Shozo Koyama; John W. Manning, Jr., both of Atlanta, Ga.; William S. Ammons, Oklahoma City, Okla.; Hector L. Santiesteban, Atlanta, Ga.

[73] Assignee: Boehringer Ingelheim International GmbH, Ingelheim, Fed. Rep. of Germany

[21] Appl. No.: 306,773

[22] Filed: Sep. 29, 1981

[51] Int. Cl.³ .......................................... A61K 31/505
[52] U.S. Cl. ................................................... 424/251
[58] Field of Search ........................................ 424/251

[56] References Cited

PUBLICATIONS

CA 81:120688z–(1974).
CA 85:13838j–(1976).

Primary Examiner—Jerome D. Goldberg
Assistant Examiner—Freda Abramson
Attorney, Agent, or Firm—Hammond & Littell, Weissenberger & Muserlian

[57] ABSTRACT

The method of treating endotoxin shock with 2,2'-[(4,8-bis(diethylamino)-pyrimido[5,4-d]pyrimidine-2,6-diyl)-di-(2-methoxyethyl)imino]diethanol or a non-toxic, pharmacologically acceptable acid addition salt thereof.

1 Claim, 4 Drawing Figures

METHOD OF TREATING ENDOTOXIN SHOCK WITH A PYRIMIDO-PYRIMIDINE DERIVATIVE

This invention relates to a novel method of treating endotoxin shock with a known pyrimido-pyrimidine derivative.

More particularly, the present invention relates to the method of treating endotoxin shock with 2,2'-[(4,8-bis(-diethylamino)-pyrimido[5,4-d]pyrimidine-2,6-diyl)di-(2-methoxyethyl)imino]diethanol (hereinafter "RA 642") of the formula

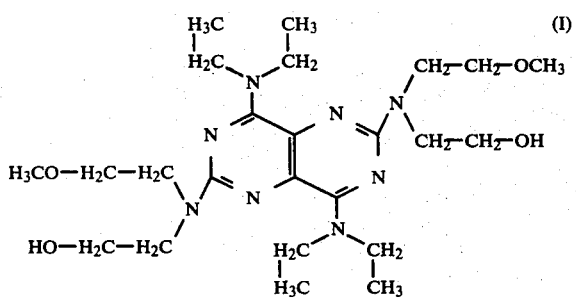

or a non-toxic, pharmacologically acceptable acid addition salt thereof.

Examples of non-toxic, pharmacologically acceptable acid addition salts of RA 642 are those formed with hydrochloric acid, hydrobromic acid, sulfuric acid, phosphoric acid, citric acid, tartaric acid, maleic acid or the like.

The preparation of RA 642 and its non-toxic, pharmacologically acceptable acid addition salts is described in Philippine Pat. No. 9640, issued on Jan. 26, 1976.

BACKGROUND OF THE INVENTION

It has been proposed that central adrenergic neurons influence peripheral sympathetic nerve activity and thus cardiovascular regulation. The stimulation of alpha adrenergic receptors in vasomotor centers mediates a decrease in blood pressure, heart rate and in peripheral sympathetic activity [Kobinger et al., Eur. J. Pharmacol. 2, 155–162 (1967); and Hausler, Naunyn-Schmiedeberg's Arch. Pharmacol. 286, 97–111 (1974)]. We have previously indicated that E. coli endotoxin may exert its hypotensive effect by activating the central autonomic blood pressure regularoty circuits, by stimulation of central alpha adrenergic receptors leading to inhibition of brain stem sympathetic pathways that participate in the baroreceptor reflex system. Furthermore, it has recently been shown that RA 642 has a central hypertensive effect acting on the medullary cardiovascular regulatory systems [Kadatz et al., Naunyn-Schmiedeberg's Arch. Pharmacol. 292, 79–103 (1976); and Kobinger et al., Naunyn-Schmiedeberg's Arch. Pharmacol. 292, 105–111 (1976)].

If the central autonomic blood pressure regulatory circuits are important to the hypotensive response to endotoxin, RA 642 may improve the hemodynamic alterations and survival rate in endotoxin shock.

DESCRIPTION OF THE INVENTION

We have now discovered that RA 642 and its non-toxic, pharmacologically acceptable acid addition salts are useful for the successful treatment of entotoxin shock in warm-blooded animals such as cats.

The novel utility of RA 642 was ascertained by the following tests.

Methods

General Procedures

16 Healthy cats weighing between 2.0 and 3.5 kg were used. Anesthesia was induced with ether and maintained with alpha chloralose (40–50 mg/kg i.v.). The cats were immobilized with gallamine triethiodide (5 mg/kg i.v.) and artificially ventilated. Body temperature was maintained between 36° C. and 37° C. The left femoral artery and vein were cannulated for blood pressure recording and drug administration, respectively.

Recording and Integration of Nerve Discharges

The left preganglionic splanchnic nerve (PSN) was approached retroperitoneally and was divided into a few multifiber strands under a dissecting microscope and covered with mineral oil. PSN discharges were recorded by means of bipolar silver electrodes at the central cut ends of the nerve. The discharges were amplified with a capacitance-coupled preamplifier (Grass P15; band width 10 Hz–3 KHz) and displayed on a dual beam oscilloscope. The neurogram was integrated by use of an R-C integrator circuit with a time constant of 0.1 second. The output signals of the integrator were calibrated in microvolts. All events were displayed on a pen recording system. The area of the integrated nerve discharges was measured by means of a planimeter (Hewlett Package; calculator 9810A, digitizer 9864A) for a given period and was expressed as PSN activity per unit time.

Drug Administration

E. coli endotoxin (Difco Lab. 0111:B4), which was freshly prepared as a suspension in physiological saline, was injected intravenously in all the cats as dosage amount of 1 mg/kg in a total volume of 1 ml. Thirty minutes after endotoxin injection, 0.25 mg/kg of RA 642 in a volume of 0.1 ml was injected intravenously into 8 cats which constituted the treated group. Another 8 cats were given only 0.1 ml of physiological saline as a vehicle 30 minutes after endotoxin injection and constituted the non-treated group.

Survival Experiment

The experiments were carried out on twelve healthy cats weighing between 2.5 and 3.5 kg, and anesthetized with pentobarbital, 35 mg/kg intramuscularly. The catheter for E. coli endotoxin and drug administration was inserted in the superficial saphenous vein below the knee joint and was kept in place for 24 hours. Thirty minutes and 6 hours after endotoxin (1 mg/kg), 0.25 mg/kg of RA 642 was injected intravenously through the catheter. Six of 12 cats served as the non-treated group and were given the same amount of saline. The animals were checked for vital signs, including the condition of stools, every three hours for 48 hours after endotoxin, and their behavior was observed for one week.

Statistical Analysis

Values for mean blood pressure, pulse pressure and PSN activity are reported as the mean percent changes ±SE from the pre-endotoxin level. Results for the time course studies were first treated with analysis of variance and then treated with paired t-test. Significant differences in survival were determined with an $X^2$ test (Yates' modification for small samples).

RESULTS

Baseline Value

Pre-endotoxin values for mean blood pressure (MBP), pulse pressure and amplitude of the integrated PSN discharges in non-treated group were $118\pm5$ mmHg, $40\pm3$ mmHg and $52.3\pm2.3$ μV, respectively. There were no statistical differences between the baseline values in the non-treated group and in the treated group (P>0.05), as shown in Table I.

TABLE I

| | Baseline Values. | | | |
|---|---|---|---|---|
| | Before Endotoxin | | 30 min. after Endotoxin | |
| | Non-treated | Treated | Non-treated | Treated |
| MBP (mmHg) | 118 ± 5 | 119 ± 6 | 79 ± 7* | 78 ± 9* |
| Pulse Pressure (mmHg) | 40 ± 3 | 38 ± 5 | 33 ± 3* | 28 ± 3* |
| Amplitude of PSN Discharges (μV) | 52.2 ± 2.3 | 55.4 ± 6.4 | 24.8 ± 6.2* | 24.9 ± 4.6* |

MBP and PSN discharges = mean blood pressure and preganglionic splanchnic nerve discharges, respectively.
*P < 0.01 in comparison with each pre-endotoxin level.

Non-treated Group

Figure 1:
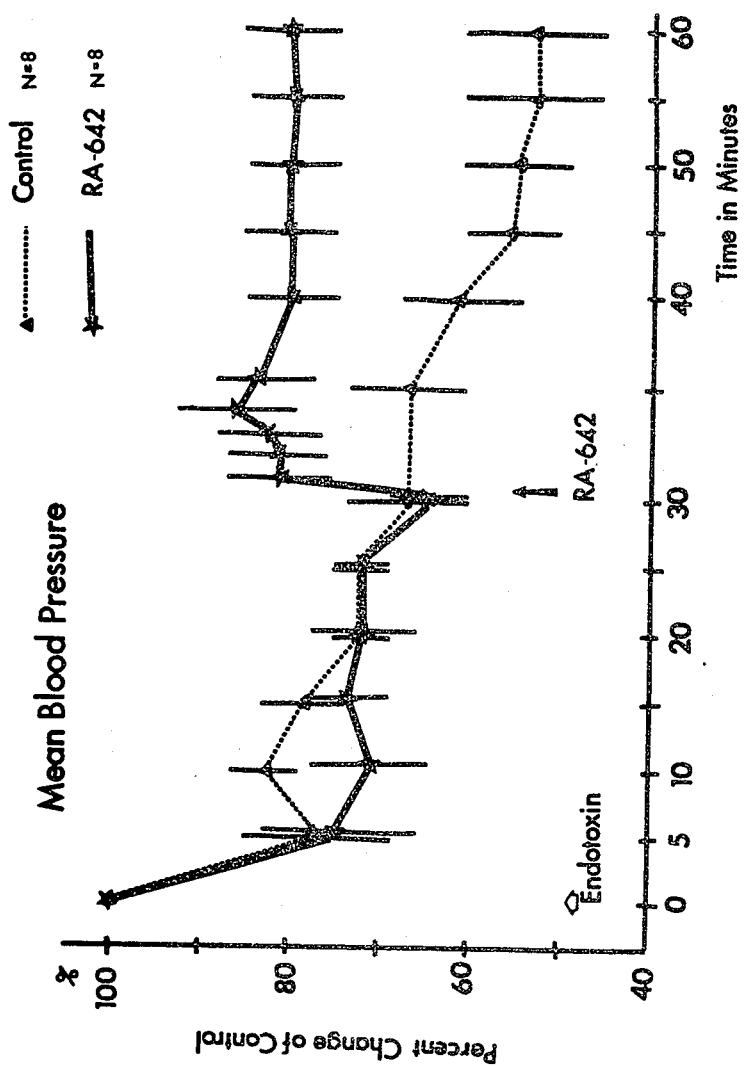
FIG. 1 shows the percent changes in mean blood pressure following endotoxin and RA 642.
Figure 2:
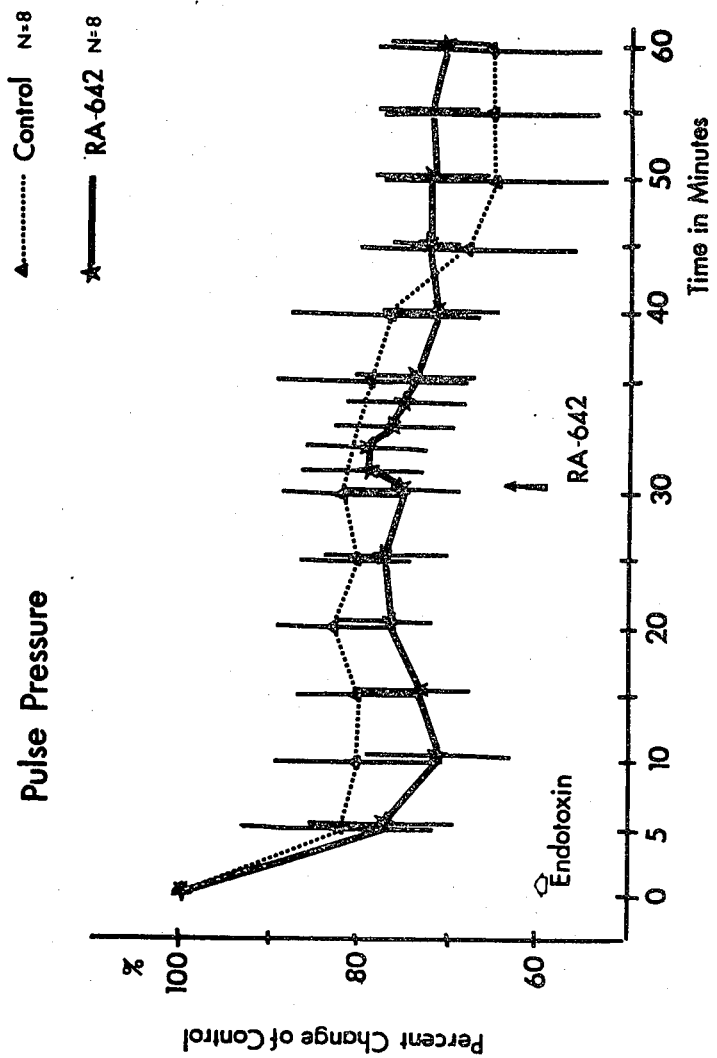
FIG. 2 shows the percent changes in pulse pressure following endotoxin and RA 642.
Figure 3:
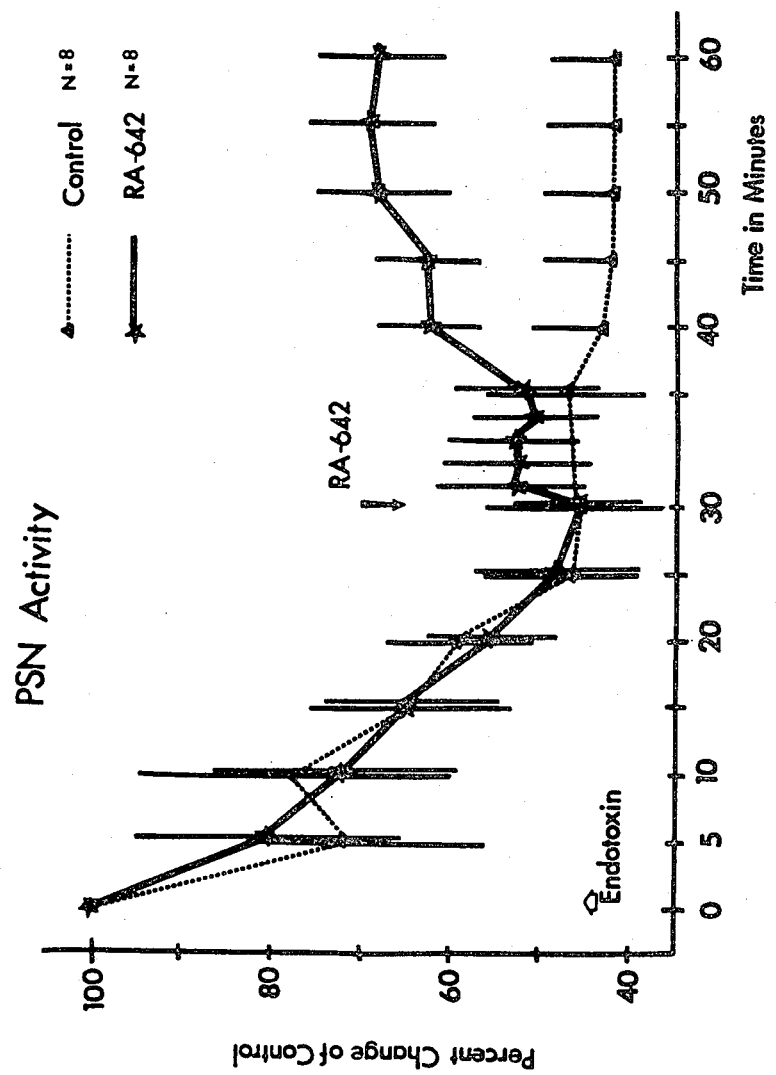
FIG. 3 shows the percent changes in PSN activity following endotoxin and RA 642.

The data for MBP, pulse pressure and PSN activity in this group are shown by the triangles connected by the dotted lines in FIG. 1, FIG. 2, and FIG. 3, respectively. Following intravenous administration of endotoxin, MBP fell to $77\pm8\%$ (P<0.01) of pre-endotoxin level (pre-E1) within 5 minutes after endotoxin injection. There followed a slight temporary recovery of MBP to $82\pm4\%$ (P<0.05) of pre-E1. There was a secondary decay in MBP so that after 30 minutes MBP reached to $68\pm7\%$ (P<0.01) of pre-E1. Following vehicle injection 30 minutes after endotoxin injection, MBP continued to decline reaching $54\pm8\%$ (P<0.01) of pre-E1 60 minutes after endotoxin (FIG. 1). The pulse pressure decreased to $82\pm11\%$ (P<0.05) of pre-E1 5 minutes after endotoxin which persisted until 30 minutes after endotoxin. Following vehicle injection the pulse pressure dropped to $78\pm11\%$ (P<0.01) of pre-E1 5 minutes after vehicle treatment. Finally, there was a gradual decline in the pulse pressure to $67\pm13\%$ (P<0.01) of pre-E1 (FIG. 2).

PSN activity decreased to $71\pm11\%$ (P<0.05 of pre-E1 within 5 minutes after endotoxin injection. After a small recovery in PSN-activity, a secondary decrease in PSN-activity reached to $47\pm10\%$ (P<0.01) of pre-E1 30 minutes after endotoxin injection. Following vehicle saline injection, PSN activity did not show any changes so that after 60 minutes, PSN activity was $42\pm8\%$ (P<0.01) of pre-E1 (FIG. 3).

Treated Group

The data for MBP, pulse pressure and PSN activity in this group are shown by the stars connected by solid lines in FIG. 1, FIG. 2 and FIG. 3, respectively. There were no significant differences in the time course of each parameter for the first 30 minutes after endotoxin injection between the two groups (P<0.05). MBP, pulse pressure and PSN activity 30 minutes after endotoxin injection were $65\pm5\%$ (P<0.01), $73\pm7\%$ (P<0.01) and $46\pm8\%$ (P<0.01) of pre-E1, respectively. These reduced levels by endotoxin were not significantly different from the levels in the non-treated group (P<0.05).

Within 5 minutes after injection of RA 642, MBP rapidly recovered to $83\pm6\%$ (P<0.05) of pre-E1. This level of MBP was significantly higher than the level at 30 minutes after endotoxin (P<0.01) and was maintained until the end of the experiment (FIG. 1). The pulse pressure did not change significantly, so that 60 minutes after endotoxin (30 minutes after treatment) pulse pressure was $70\pm6\%$ (P<0.01) of pre-E1. There was no significant difference in the time course of changes in pulse pressure after treatment between both groups (P<0.05) (FIG. 2).

Following injection of RA 642, PSN activity rapidly increased to $62\pm10\%$ (P<0.01) of pre-E1 10 minutes after treatment. This increased PSN activity by RA 642 was significantly higher than the level at 30 minutes after endotoxin (P<0.01) and was maintained until the end of the experiment. There was statistically significant difference in the time course between the non-treated group and the treated group (P<0.01) (FIG. 3).

Figure 4:
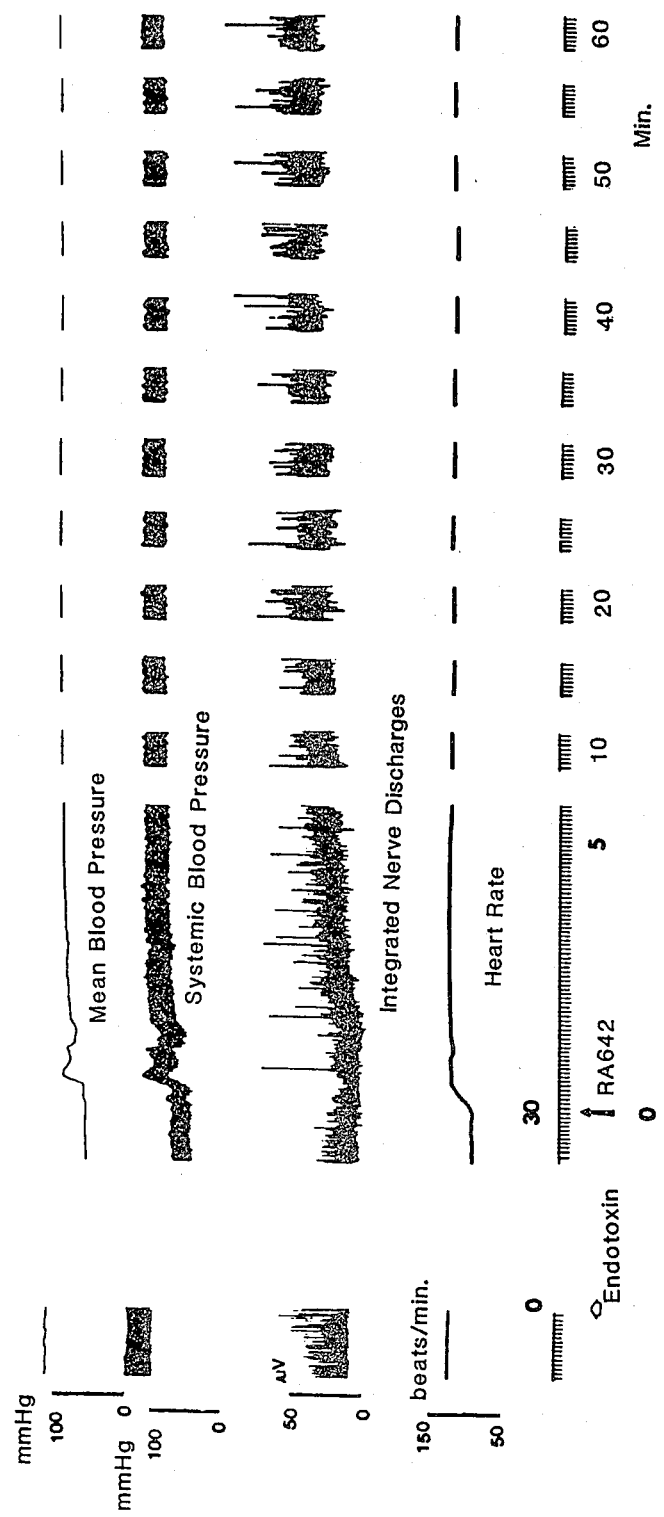
FIG. 4 shows the effects of RA 642 on blood pressure and sympathetic nerve activity. From top to bottom: mean blood pressure, systemic blood pressure and integrated nerve discharges.

FIG. 4 is an example of the pattern of response to RA 642 following intravenous injection of E. coli endotoxin.

Survival

Five of the six cats in the non-treated group (83%) died within 48 hours after endotoxin injection (average $28.7\pm2.9$ hours). Three of the six cats had bloody diarrhea. The surviving one only recovered normal appetite and behavior 4 days after endotoxin injection. In contrast, all of the 6 cats treated with RA 642 (100%) survived, as shown in Table II.

TABLE II

Effects of RA 642 on survival and condition of stool during endotoxin shock.

| | Survival | Mortality | Bloody Diarrhea | Mucous Diarrhea |
|---|---|---|---|---|
| Non-treated group (n = 6) | 1 | 5 | 3 | 2 |
| Treated group (n = 6) | 6* | 0* | 0 | 3 |

Values are number of animals in each group (n = 6)
*P < 0.05 in comparison with non-treated group.

Immediately after injection of RA 642, the animals showed deep regular breathing and an increase in muscle tonus. The corneal reflex and the reflex movements of limbs to pain stimuli were facilitated. Three of the treated cats showed a mucous diarrhea without blood during the initial period (6 hours after endotoxin). Within 48 hours after endotoxin injection, normal appetite and behavior returned in all treated animals. During the observation period, the animals treated with RA 642 did not show any signs of clonic or tonic convulsions.

For pharmaceutical purposes RA 642 or a non-toxic acid addition salt thereof is administered parenterally to warm-blooded animals suffering from endotoxin shock as the active ingredient in customary pharmaceutical compositions, that is, compositions consisting essentially of an inert pharmaceutical carrier and an effective amount of the active ingredient, such as injectable solutions or the like. The effective dosage range of RA 642 and its non-toxic acid addition salts is from 0.1 to 1.0 mgm/kg body weight, depending upon the severity of the shock.

We claim:

1. The method of treating endotoxin shock in a warm-blooded animal in need thereof, which comprises parenterally administering to said animal an effective amount for treating endotoxin shock of 2,2'-[(4,8-bis(diethylamino)-pyrimido[5,4-d]-pyrimidine-2,6-diyl)di-(2-methoxyethyl)imino]diethanol or a non-toxic, pharmacologically acceptable acid addition salt thereof.

* * * * *